(12) United States Patent
Uber (10) Patent No.: US 7,106,445 B2
(45) Date of Patent: Sep. 12, 2006

(54) PHOTOACOUSTIC GAS SENSOR UTILIZING DIFFUSION

(75) Inventor: Robert E. Uber, Pittsburgh, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 306 days.

(21) Appl. No.: 10/635,270

(22) Filed: Aug. 6, 2003

(65) Prior Publication Data

US 2005/0030539 A1   Feb. 10, 2005

(51) Int. Cl.
    *G01N 21/00* (2006.01)
(52) U.S. Cl. .................. 356/432; 356/437; 73/24.02
(58) Field of Classification Search ........ 356/432–440; 73/24.01, 587, 24.02
    See application file for complete search history.

(56) References Cited

U.S. PATENT DOCUMENTS

| 3,727,050 | A |   | 4/1973  | Kerr |
| 4,200,399 | A |   | 4/1980  | Kimble et al. |
| 4,324,632 | A | * | 4/1982  | Tantram et al. .............. 204/415 |
| 4,372,149 | A |   | 2/1983  | Zharov |
| 4,399,689 | A |   | 8/1983  | Bechthold |
| 4,740,086 | A |   | 4/1988  | Kunz et al. |
| 6,006,585 | A | * | 12/1999 | Forster ...................... 73/24.01 |

FOREIGN PATENT DOCUMENTS

| EP | 0 478 136 | 4/1992 |
| EP | 0 590 813 | 4/1994 |
| EP | 0 801 296 | 10/1997 |

* cited by examiner

*Primary Examiner*—Hoa Q. Pham
(74) *Attorney, Agent, or Firm*—James G. Uber (57) ABSTRACT

The present invention relates to a photoacoustic gas sensor utilizing diffusion having a sensing volume and an acoustic pressure sensor volume containing an acoustic pressure sensor such that the fluid connection between the sensing volume and the acoustic pressure sensor volume restricts the flow of analyte gas therethrough but does not restrict the transmission of the photoacoustic signal therethrough.

16 Claims, 6 Drawing Sheets

Figure 1

Prior Art

Figure 2

Prior Art

Figure 3

Prior Art

PHOTOACOUSTIC GAS SENSOR UTILIZING DIFFUSION

FIELD OF INVENTION

The present invention relates generally to photoacoustic gas sensors utilizing diffusion and more particularly, to devices and methods for reducing the initial response time and increasing the signal-to-noise ratios in photoacoustic gas sensors utilizing diffusion.

BACK OF THE INVENTION

The use of gas sensors to detect the concentration level of a gaseous analyte (i.e., species of interest) using the photoacoustic effect is well known. For example, U.S. Pat. No. 4,740,086 teaches the use of a photoacoustic gas sensor to convert the optical energy of an amplitude modulated light source into acoustic energy when the light excites the gaseous analyte. Sound/pressure waves of an intensity corresponding to the concentration level of the analyte gas within the sensing volume or sensing chamber are generated as the optical energy of the light incident upon the sensing chamber is, upon absorption by the analyte gas, converted into raised energy levels of the analyte gas, causing thermal/mechanical excitation of the analyte gas. These sound/pressure waves are detected by a pressure sensor or an acoustic detector such as a microphone. Typically, these devices operate in the frequency range of 2 Hz–100 Hz with 8 Hz–15 Hz being a preferred frequency range.

Figure 1:
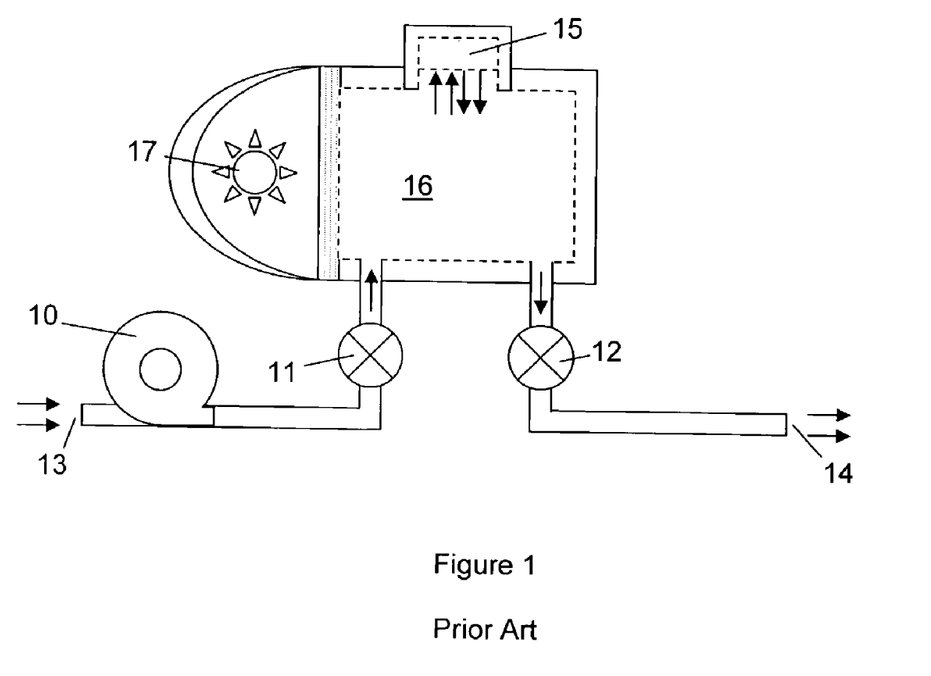
FIG. 1 shows a known pumped photoacoustic gas detector with the microphone forming part of the wall of the sensing volume.

A means to allow analyte gas to enter the sensing chamber is required. In one type of known photoacoustic detector, such as is shown in FIG. 1, the gas exchanger may consist of a pump 10 and alternately closable valves 11 and 12. This is a photoacoustic detector utilizing pumped or forced analyte gas flow from the analyte gas inlet 13 to the analyte gas outlet 14. If alternately closeable valves 11 and 12 are used, the fastest response time is obtained with the microphone 15 located in the sensing volume 16. Typically, the microphone 15 forms part of the wall of the sensing volume 16. The initial response time of such photoacoustic detectors is usually limited by the pumped flow rate of the analyte gas and the size of the sensing volume 16. Locating the microphone 15 in the wall of the sensing volume 16, however, has the disadvantage that the microphone 15 can absorb part of the light from the light source 17 incident upon the sensing chamber 16 and generate a photoacoustic signal in the absence of any analyte gas.

Figure 2:
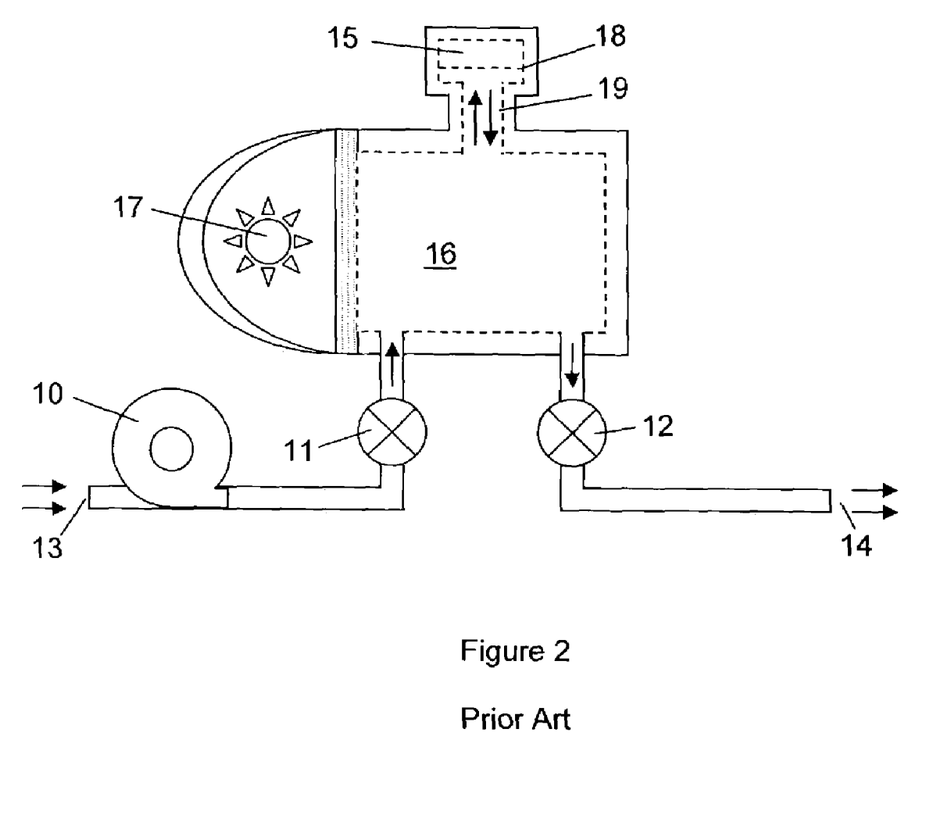
FIG. 2 shows a known pumped photoacoustic gas detector with the microphone separated from the sensing volume.

In another type of known photoacoustic detector, such as shown in FIG. 2, the gas exchanger still consists of a pump 10 and alternately closeable valves 11 and 12, but the microphone 15 is located in a separate microphone volume 18 to reduce the amount of incident light falling on the microphone 15. This type of detector has a slower initial response time than the detector shown in FIG. 1 because the analyte gas cannot move as freely from the sensing volume 16 to the microphone volume 18. To encourage the gas exchange between the sensing volume 16 and the separate microphone volume 18, the connecting hole 19 is made as large as possible to enable the analyte gas to move into the separate microphone volume 18 as quickly as possible. The size of the connecting hole 19 is a balance between the conflicting goals of a large size for fast analyte gas transfer and yet not so large that too much incident light reaches the microphone 15.

Figure 3:
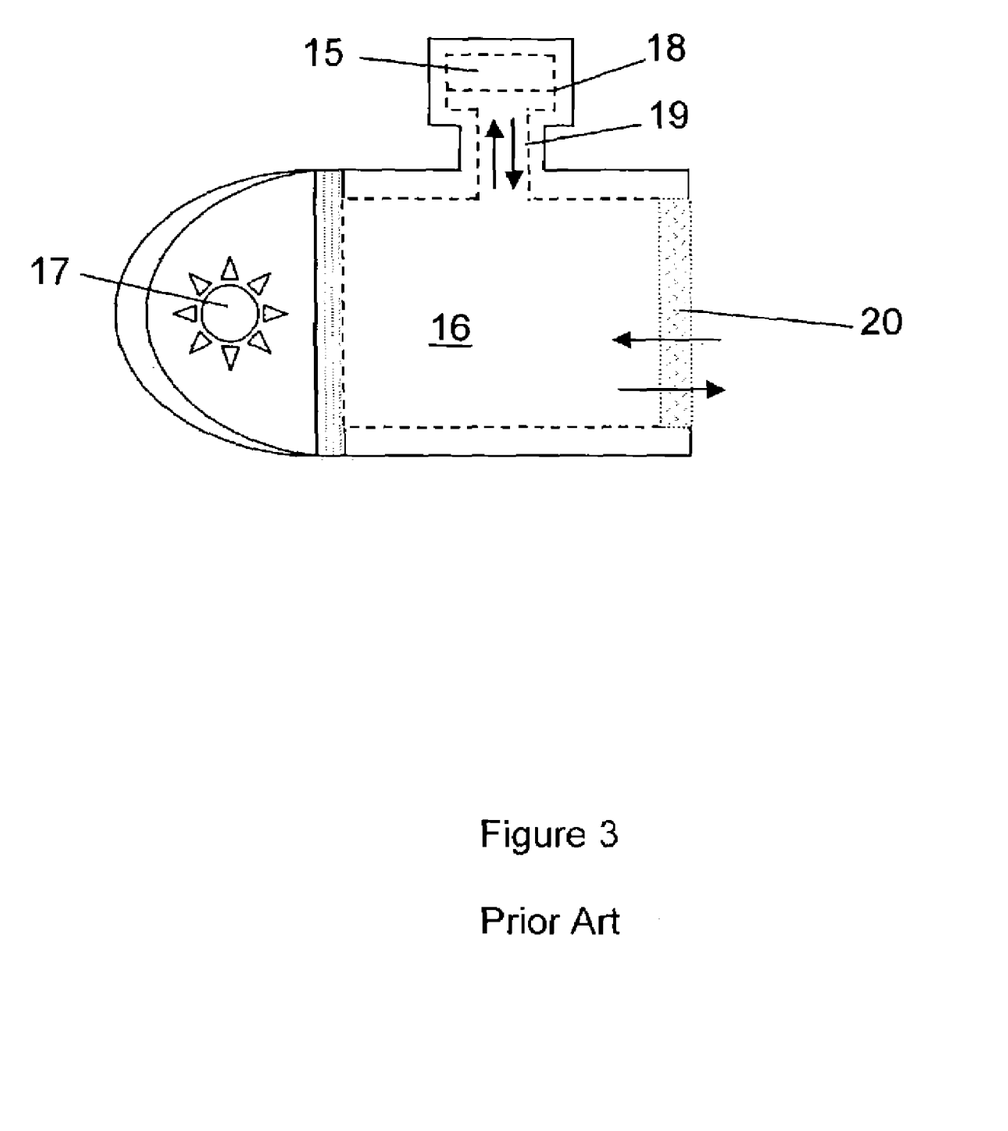
FIG. 3 shows a known photoacoustic gas detector utilizing diffusion with the microphone separated from the sensing volume.

In another type of known photoacoustic detector, the gas exchanger may include an acoustically attenuating element 20 at a gas collection point that is continuously permeable to gases, including the analyte gas. This is a photoacoustic detector utilizing diffusion and is shown in FIG. 3. The output signal of such a photoacoustic detector, however, is susceptible to noise created by interference from outside sources of sound/pressure waves, such as wind, building ventilation systems, and other vibration and acoustic phenomena. For example, porous members such as sintered metal frits through which gas relatively readily diffuses, but which attenuate the effect of external sound/pressure waves, are often placed at the entrance of diffusive photoacoustic gas sensors. Introduction of such an acoustic pressure attenuating element to reduce noise, however, typically results in a corresponding loss of responsiveness to changing signal levels. One must balance this attenuating effect and its corresponding decrease in noise against the resulting increase in initial response time. For example, the specification for combustible gas detectors of the Instrument Society of America (ISA) requires a gas concentration level measurement stability at wind speeds of up to 5 meters per second (m/s) with a corresponding initial response time (to 60% of full scale indication) of less than 12 seconds. One method to reduce such noise is to incorporate some means of attenuating extraneously generated sound pressure waves such as is described in U.S. patent application Ser. No. 09/611,384 filed Jul. 7, 2000 of Moeckli et al., the disclosure of which is incorporated herein by reference.

However, if a diffusion photoacoustic detector is used, the initial response time is typically limited by the diffusion rate of the analyte gas through the acoustic pressure attenuating element 20. This diffusion rate is generally much slower than the analyte gas flow rate that occurs in a pumped photoacoustic detector. Thus the use of a microphone 15 in a separate microphone volume 18 with a large connecting hole 19 (such as is used in pumped detectors with valves) will actually lead to an even slower initial response time in a diffusion photoacoustic detector because both the sensing volume 16 and the separate microphone volume 18 must fill with analyte gas before an accurate reading can be obtained.

It would be very desirable, however, to develop devices and methods that increase the signal-to-noise ratios in photoacoustic detectors utilizing diffusion while maintaining a satisfactory initial response time for such detectors. Also, it would be very desirable to develop devices and methods that reduce the initial response time while maintaining acceptable signal-to-noise ratios in photoacoustic detectors utilizing diffusion which, through signal processing, allows the gas sensor characteristics to be optimized for each application.

SUMMARY OF THE INVENTION

Generally, the present invention provides a method and device for controlling the diffusion of the analyte gas within a diffusive photoacoustic gas sensor to improve the response time of the sensor. The photoacoustic gas sensor or detector of the present invention comprises a sensing volume and an acoustic pressure sensor volume. The sensing volume is in fluid connection with the environment through an acoustic pressure attenuating element such that the analyte gas can diffuse into the sensing volume through the acoustic pressure attenuating element. The acoustic pressure sensor volume is in fluid connection with the sensing volume such that the transfer or transmission of the photoacoustic pressure signal therebetween is not adversely affected or significantly limited while at the same time the rate of analyte gas diffusion into the acoustic pressure sensor volume is controlled; for example, restricted, hindered, slowed and/or blocked, such that it is less than the rate of analyte gas diffusion from the environment into the sensing volume. As a result, the initial response time of the photoacoustic sensor, both rising and falling, will be based only on the time for the analyte gas to diffuse into or out of the sensing volume, and not on the time for the analyte gas to diffuse into or out of the combined volume of the sensing volume and the acoustic pressure sensor volume. Thus the response time of the photoacoustic sensor is independent of the size of the acoustic pressure sensor volume relative to the size of the sensing volume. Preferably, a faster initial rise time to T50 and T90 can be achieved by restricting, limiting, hindering or controlling the analyte diffusion to the acoustic pressure sensor volume.

In a preferred embodiment of the present invention, the analyte gas diffusion between the sensing volume and the acoustic pressure sensor volume occurs in close proximity to and preferably adjacent to the source of the analyte gas diffusion from the environment into the sensing volume. Preferably, the connection between the sensing volume and the acoustic pressure sensor volume is located in or near a corner or edge of the sensing volume adjacent to the source of the analyte gas diffusion from the environment into the sensing volume so that the small amount of gas diffusion that does occur through the connection has the least photoacoustic effect.

Other details, objects and advantages of the present invention will be more readily apparent from the following description of a presently preferred embodiment thereof.

BRIEF DESCRIPTION OF THE DRAWINGS

In the accompanying drawings, a preferred embodiment of the present invention is illustrated, by way of example only, wherein.

DESCRIPTION OF THE PREFERRED EMBODIMENTS

Figure 4:
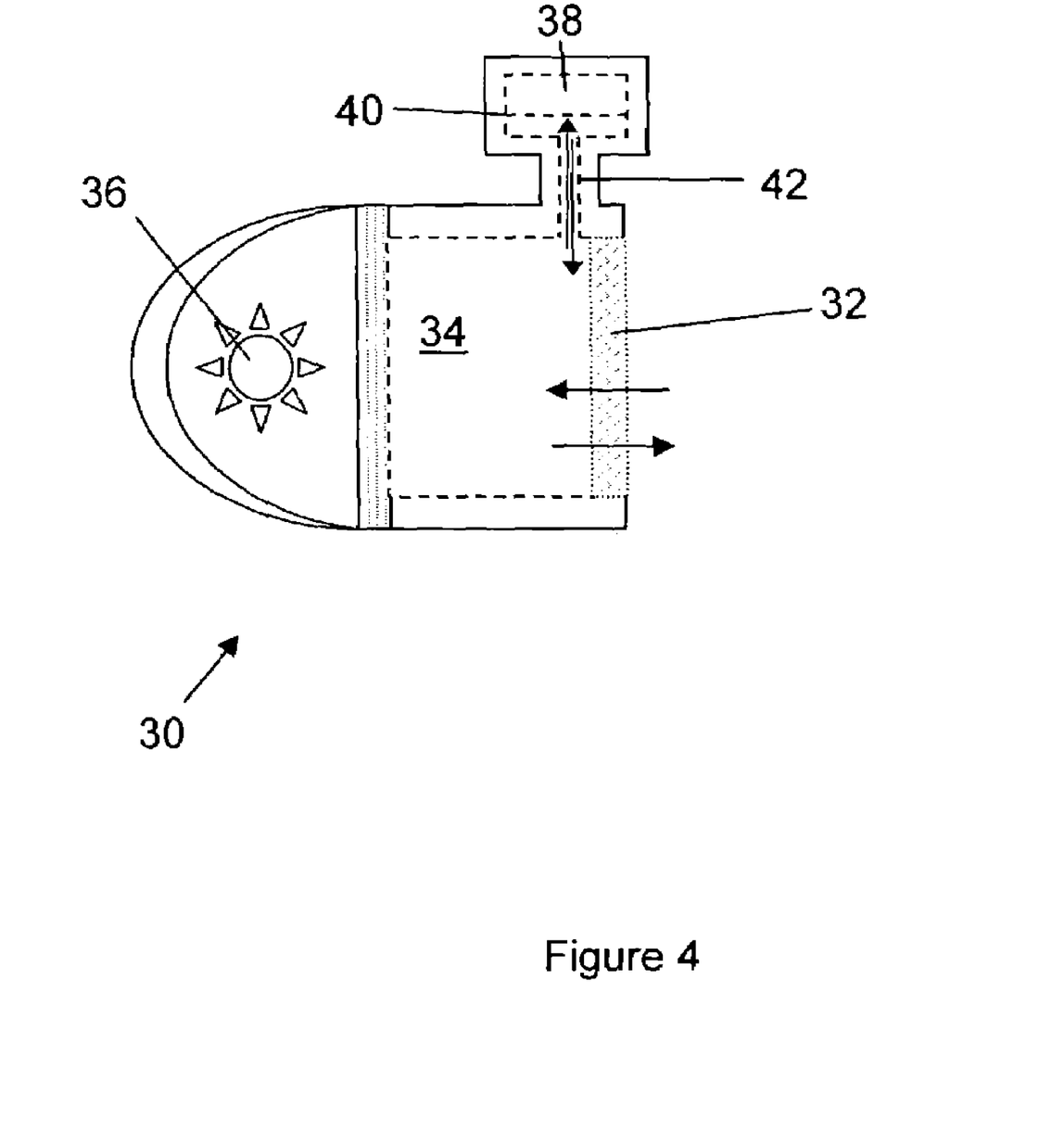
FIG. 4 shows a photoacoustic gas detector of the present invention utilizing a capillary tube.

A preferred embodiment of a diffusive photoacoustic gas detector 30 of the present invention is illustrated in FIG. 4. Reference is made to U.S. Pat. No. 4,740,086, the disclosure of which is incorporated by reference as if fully set forth herein, for the principles of operation and construction of a photoacoustic sensor/detector. In the embodiment of FIG. 4, an acoustically attenuating element 32 that is continuously permeable to an analyte gas makes up a portion of the wall of the sensing volume 34. As is known in the art, the acoustically attenuating element 32 acts to reduce external sources of sound/pressure waves from entering the sensing volume 34 and acts to ensure that the resulting photoacoustic pressure signal is not weakened by the escape of such signal from the sensing volume 34 while offering only minimal resistance to the diffusion of the analyte gas into the sensing volume 34. Preferably, the optical energy from the light source 36 enters through another portion of the wall of the sensing volume 34.

To reduce the amount of light falling thereon, the acoustic sensor 38 (typically a microphone), is located in a separate acoustic pressure sensor volume 40. The acoustic pressure sensor volume 40 includes volumes both internal and external to the acoustic pressure sensor. The acoustic sensor pressure volume 40 is in fluid connection with the sensing volume 34 through a connector 42 such that the photoacoustic signal generated by the light striking the analyte gas in the sensing volume 34 is transmitted to the acoustic pressure sensor 38 with very little, if any, loss of signal. Thus, the photoacoustic pressure signal is not substantially restricted, hindered, blocked or otherwise adversely affected by the connector 42.

However, the connector 42 between the acoustic pressure sensor volume 40 and the sensing volume 34 does limit the rate of the analyte gas diffusion into the acoustic pressure sensor volume 40. Preferably, the rate is limited such that it is much less than the rate of analyte gas diffusion from the environment into the sensing volume 34. The cross-sectional area and the length of the connector 42 between these volumes are both important in controlling and limiting the analyte gas diffusion. They should be chosen such that one obtains a capillary effect. This typically occurs when the diameter is generally less than 1 mm and the ratio of the length to the diameter is greater than 10. One preferred embodiment of connector 42 is a first tube about 0.5 mm in diameter and about 4 mm long connected to a second tube about 1 mm in diameter and about 7 mm long. Another preferred connector is a hollow metal needle or tube or. catheter having dimensions such that capillary diffusion occurs. Preferably, the connector 42 between the acoustic pressure sensor volume 40 and the sensing volume 34 acts as a capillary tube that restricts, limits, hinders and/or controls the flow/diffusion of the analyte gas. Diffusion through a capillary is discussed in U.S. Pat. Nos. 4,132,616 and 4,324,632, the disclosures of which are incorporated therein by reference.

Figure 5:
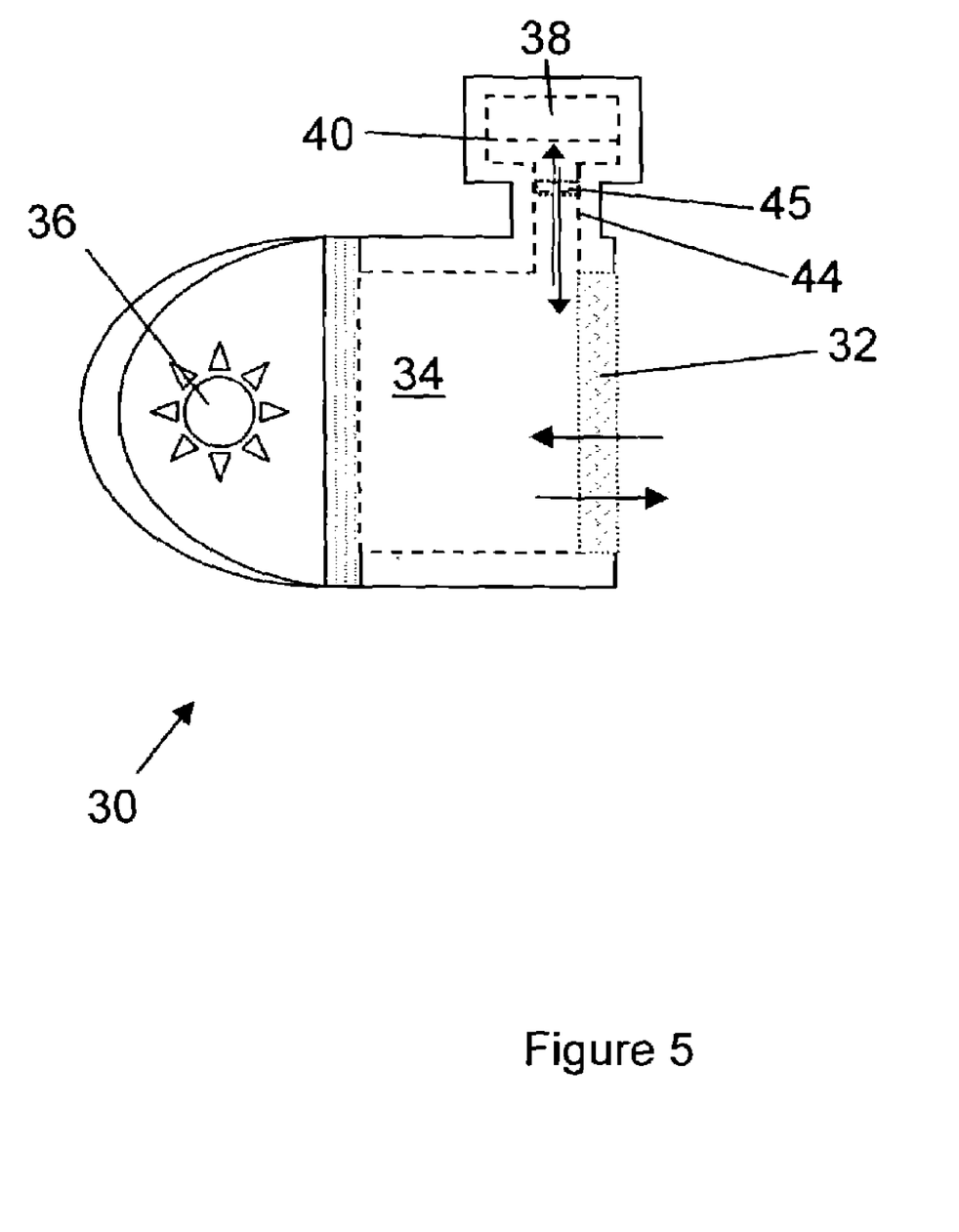
FIG. 5 shows a photoacoustic detector of the present invention utilizing a flexible membrane.

Another preferred embodiment of a diffusive photoacoustic gas detector 30 of the present invention is illustrated in FIG. 5. In FIG. 5 a membrane 45 is used to restrict, limit, hinder, block or control the analyte gas diffusion between the sensing volume 34 and the acoustic pressure sensor volume 40. Preferably, the membrane 45 is flexible so that it does not significantly affect the transmission of the photoacoustic signal therethrough. It also should not allow light to penetrate it. An example of such a membrane is one made of polytetrafluoroethylene and sold under the Brand Name GORTEX. With such a membrane, the connector 44 does not have to be as small as a capillary but can be similar in size to hole 19.

Figure 6:
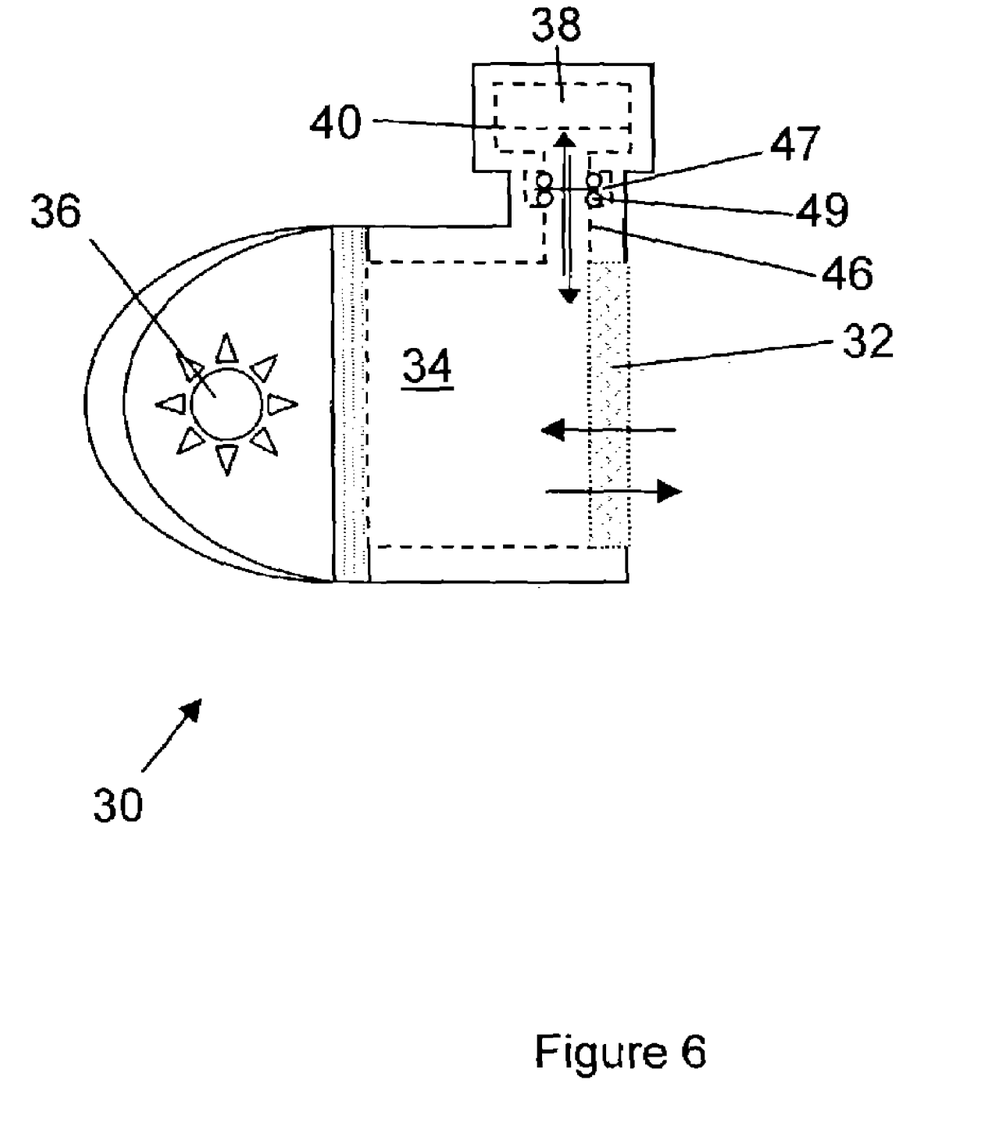
FIG. 6 shows a photoacoustic detector of the present invention utilizing a rigid membrane in a flexible support.

Another preferred embodiment of a diffusive photoacoustic gas detector 30 of the present invention is illustrated in FIG. 6. In FIG. 6, a rigid membrane 47 (preferably one made of thin metal) is used to restrict, limit, hinder, block or control the analyte gas diffusion between the sensing volume 34 and the acoustic pressure sensor volume 40. The membrane 47 is mounted in a flexible support 49 that permits the membrane 47 to move so as not to significantly affect the transmission of the photoacoustic signal therethrough. Preferably support 49 can be two O rings which are flexible enough to permit rigid membrane 47 to move and thereby transmit the photoacoustic signal. Membrane 47 preferably has a tiny hole in it (on the order of 20 microns) to permit steady-state pressure equalization. With such a membrane, the connector 46 does not have to be as small as a capillary, but can be similar in size to hole 19.

One benefit of the present invention is that the initial response time, either rising or falling, can be made independent of the size of the acoustic pressure sensor volume 40 relative to the size of the sensing volume 34. The sensing volume 34 can then be reduced with a corresponding reduction in the initial response time because of the increased ratio of the surface area of the acoustically attenuating element 32 to the sensing volume 34, without the resulting slowing or dilution effect typically caused by the acoustic pressure sensor volume 40. A preferred embodiment is for the sensing volume 34 to be similar in size or even smaller than the acoustic pressure sensor volume 40. With a faster initial response time, the photoacoustic detector 30 can have more signal averaging performed on it to achieve higher signal-to-noise ratios.

Preferably, the fluid connector (42, 44 or 46) between the sensing volume 34 and the acoustic pressure sensor volume 40 is placed in close proximity to and preferably adjacent to the source of the analyte gas diffusion from the environment into the sensing volume (i.e., the acoustic pressure attenuating element 32) so that the small amount of gas diffusion that does occur through the connector has the least effect when compared to the diffusion through the acoustic pressure attenuating element 32.

More preferably, the connector (42, 44 or 46) between the sensing volume 34 and the acoustic pressure sensor volume 40 is located in or near a corner or edge of the sensing volume 34 adjacent to the acoustic pressure attenuating element 32 so that the small amount of analyte gas diffusion that does occur through the connector has the least photoacoustic effect. The photoacoustic effect near the walls, corners or edges of the sensing volume 34 is already reduced by a portion of the raised energy state of the analyte gas losing some of its energy directly to the sensing volume wall by collision therewith rather than by collision with other gas or air molecules thus transferring the energy as thermal and then as pressure or acoustical energy.

While a presently preferred embodiment of practicing the invention has been shown and described with particularity in connection with the accompanying drawings, the invention may otherwise be embodied within the scope of the following claims.

What is claimed is:

1. A photoacoustic detector for measuring an analyte gas in an environment, the photoacoustic detector comprising:
   a source of optical energy;
   a sensing volume, the sensing volume being in fluid connection with the environment through an acoustic pressure attenuating element such that the analyte gas can diffuse into the sensing volume through the acoustic pressure attenuating element; and
   an acoustic pressure sensor volume including an acoustic pressure sensor, the acoustic pressure sensor volume being in fluid connection with the sensing volume through a capillary tube such that the initial response time of the photoacoustic detector is independent of the size of the acoustic pressure sensor volume relative to the size of the sensing volume.

2. The photoacoustic detector of claim 1 wherein the fluid connection between the acoustic pressure sensor volume and the sensing volume is placed in close proximity to the acoustic pressure attenuating element.

3. The photoacoustic detector of claim 1 wherein the fluid connection between the acoustic pressure sensor volume and the sensing volume is placed near a corner of the sensing volume in close proximity to the acoustic pressure attenuating element.

4. The photoacoustic detector of claim 1 wherein the fluid connection between the acoustic pressure sensor volume and the sensing volume is placed near an edge of the sensing volume in close proximity to the acoustic pressure attenuating element.

5. The photoacoustic detector of claim 1 wherein the diffusion rate of the analyte gas from the sensing volume into the acoustic pressure sensor volume through the fluid connection is less than the diffusion rate of the analyte gas from the environment into the sensing volume through the acoustic pressure attenuating element.

6. The photoacoustic detector of claim 1 wherein the sensing volume and the acoustic pressure sensor volume are similar in size.

7. The photoacoustic detector of claim 1 wherein the sensing volume is less than the acoustic pressure sensor volume.

8. The photoacoustic detector of claim 1 wherein the sensing volume is larger than the acoustic pressure sensor volume.

9. A photoacoustic detector for measuring an analyte gas in an environment, the photoacoustic detector comprising:
   a source of optical energy;
   a sensing volume, the sensing volume being in fluid connection with the environment through an acoustic pressure attenuating element such that the analyte gas can diffuse into the sensing volume through the acoustic pressure attenuating element;
   an acoustic pressure sensor volume similar in size to the sensing volume and including an acoustic pressure sensor; and
   a connector between the acoustic pressure sensor volume and the sensing volume such that the diffusion of the analyte gas from the sensing volume to the acoustic pressure sensor volume is controlled without adversely affecting the transmission of the photoacoustic pressure signal between the sensing volume and the acoustic pressure sensor volume.

10. The photoacoustic detector of claim 9 wherein the connector between the acoustic pressure sensor volume and the sensing volume functions as a capillary tube.

11. The photoacoustic detector of claim 9 wherein the connector between the acoustic pressure sensor volume and the sensing volume is placed in close proximity to the acoustic pressure attenuating element.

12. The photoacoustic detector of claim 9 wherein the connector between the acoustic pressure sensor volume and the sensing volume is placed near a corner of the sensing volume in close proximity to the acoustic pressure attenuating element.

13. The photoacoustic detector of claim 9 wherein the connector between the acoustic pressure sensor volume and the sensing volume is placed near an edge of the sensing volume in close proximity to the acoustic pressure attenuating element.

14. The photoacoustic detector of claim 9 wherein the diffusion rate of the analyte gas from the sensing volume into the acoustic pressure sensor volume through the connector is less than the diffusion rate of the analyte gas from the environment into the sensing volume through the acoustic pressure attenuating element.

15. The photoacoustic detector of claim 9 wherein the connector between the acoustic pressure sensor volume comprises a gas permeable flexible membrane.

16. The photoacoustic detector of claim 9 wherein the connector between the acoustic pressure sensor volume and the sensing volume comprises a rigid membrane mounted in a flexible support and having a hole therein to permit steady-state pressure equalization.

* * * * *